(12) United States Patent
Mizutani et al.

(10) Patent No.: US 6,431,743 B1
(45) Date of Patent: Aug. 13, 2002

(54) METHOD OF PREPARING AND EXTRUDING A CHEMICAL AGENT USING A KNEADER AND CHEMICAL-AGENT EXTRUSION ASSISTING TOOL

(75) Inventors: Yoichiro Mizutani; Takenori Sawamura; Masateru Hattori; Masahiko Okuyama, all of Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 16 days.

(21) Appl. No.: 09/678,399

(22) Filed: Oct. 3, 2000

(30) Foreign Application Priority Data

Oct. 6, 1999 (JP) .......................................... 11-285919

(51) Int. Cl.⁷ ................................................. B01F 15/02
(52) U.S. Cl. ...................... 366/189; 366/195; 366/247; 222/327; 606/93
(58) Field of Search ................................ 366/130, 139, 366/189, 194–196, 244–247, 348; 222/325–327, 386, 390; 606/92–94

(56) References Cited

U.S. PATENT DOCUMENTS

| 3,417,971 A | | 12/1968 | Blank et al. |
| 3,724,077 A | | 4/1973 | Preston et al. |
| 4,671,263 A | | 6/1987 | Draenert |
| 4,751,921 A | | 6/1988 | Park |
| 4,906,231 A | * | 3/1990 | Young |
| 5,551,778 A | | 9/1996 | Hauke et al. |
| 5,588,745 A | * | 12/1996 | Tanaka et al. |
| 5,624,260 A | | 4/1997 | Wilcox et al. |
| 5,842,786 A | * | 12/1998 | Solomon |
| 5,876,116 A | * | 3/1999 | Barker et al. |
| 6,086,594 A | | 7/2000 | Brown |

FOREIGN PATENT DOCUMENTS

| DE | 40 22 986 A1 | 1/1992 |
| DE | 195 32 015 A1 | 3/1997 |
| EP | 0 445 951 A2 | 9/1991 |
| EP | 0 692 229 A1 | 1/1996 |
| FR | 310146 | * 4/1989 |
| FR | 2 716 375 A1 | 8/1995 |
| FR | 2 720 268 A1 | 12/1995 |
| GB | 2 338 428 A1 | 12/1999 |
| JP | 5-317333 | 12/1993 |
| JP | 7-255748 | 10/1995 |
| WO | WO86/06618 A1 | 11/1986 |
| WO | WO94/16951 A1 | 8/1994 |
| WO | WO 95/00078 | 1/1995 |
| WO | WO97/21485 A1 | 6/1997 |

\* cited by examiner

Primary Examiner—Charles E. Cooley
(74) Attorney, Agent, or Firm—Sughrue Mion, PLLC

(57) ABSTRACT

An assisting tool for pressing a piston while fixing in place a syringe or a similar instrument which contains a highly viscous chemical agent, so as to extrude the chemical agent, as well as a method for extruding a chemical agent using the same. The chemical-agent extrusion assisting-tool includes a tool body in the form of a cylindrical body having a space formed therein for accommodating a tubular container, such as a syringe, which contains a highly viscous chemical, such as calcium-phosphate-based cement formed by kneading a calcium phosphate powder and a kneading liquid composed of a polysaccharide-containing aqueous solution, and an outlet formed at its bottom end. The cylindrical body has a cylindrical space formed therein so as to open at an upper end surface thereof. The assisting-tool further has a pusher including a handle portion for pressing a piston to be inserted into the tubular container, and a tubular body screw-threadedly engaged with the tool body and disposed on a side of the handle portion which presses the piston. The handle portion of the chemical-agent extrusion assisting-tool is rotated so as to press the tubular body into the cylindrical space and so as to press the piston into the tubular container, thereby extruding the chemical agent from the tubular container.

3 Claims, 8 Drawing Sheets

METHOD OF PREPARING AND EXTRUDING A CHEMICAL AGENT USING A KNEADER AND CHEMICAL-AGENT EXTRUSION ASSISTING TOOL

BACKGROUND OF THE INVENTION

1. Field of the Invention

The present invention relates to a chemical-agent extrusion assisting-tool adapted for use in extruding a highly viscous chemical agent from a syringe barrel or a similar container through, for example, an injection needle or a catheter, as well as to a method for extruding a chemical agent using the chemical-agent extrusion assisting-tool. The chemical-agent extrusion assisting-tool of the present invention facilitates extrusion of a highly viscous chemical agent such as bone cement through, for example, an injection needle connected to a syringe barrel. The chemical agent extrusion assisting-tool of the present invention is thus useful in filling bon e cement, such as calcium-phosphate-based cement, into a defective portion of an organic bone caused by bone fracture or osteoporosis or in applying the same for serving as an adhesive for bonding an artificial bone, formed from metal or ceramic, to an organic bone. The invention also relates to a method for extruding a chemical agent using the chernical-agent extrusion assisting-tool, a kneader for use in preparing the chemical agent and to form the container from which the chemical agent is to be extruded using the chemical-agent extrusion assisting-tool. Further, the invention relates to a method for preparing and extruding a chemical-agent using the kneader and the chemical agent extrusion assisting-tool.

2. Description of the Related Art

A gun-type ejector for aqueous paste dental materials (Japanese Patent Application Laid-Open (kokai) No. 7-255748 and PCT International Application Laid-Open No. W095/00078) is known as an instrument for extruding through, for example, an injection needle or a catheter, a chemical agent which is so viscous that the user encounters difficulty in extruding by pressing with his/her fingers. A gun-type ejector has also been developed for resin-based bone cement such as polymethyl methacrylate (PCT International Application Laid-Open No. W094/16951). Further, an ejector has been proposed combined with a pressurizing device such as a compressor (Japanese Patent Application Laid-Open (kokai) No. 5-317333) for calcium-phosphate-based cement, which is a highly viscous sludge-like kneaded substance and which requires a particularly high pressure for extrusion thereof.

However, these ejectors, particularly the ejector combined with a compressor, are of complicated structure and large size and are thus not readily usable. Since ejectors for extruding bone cement in the course of a surgical operation must be sterilized, they are preferably disposable. The ejectors described in the above publications are disadvantageous in terms of cost and size. Further, a gun-type ejector conventionally used for extruding dental materials and resin-based bone cement has an outlet of relatively large diameter and is thus not suited for fine-extrusion applications, such as local filling or application of chemical agent.

SUMMARY OF THE INVENTION

It is therefore an object of the present invention to solve the above-mentioned problems of conventional ejectors, and to provide a chemical-agent extrusion assisting-tool enabling extrusion of a highly viscous chemical agent such as calcium-phosphate-based cement through an outlet of small diameter such as an injection needle and capable of being of a disposable type, as well as to provide a method for completely extruding a chemical agent, by use of the assisting tool, from a syringe barrel or a similar container through, for example, an injection needle or catheter connected thereto.

A chemical-agent extrusion assisting-tool in a first aspect of the invention comprises: a tool body in the form of a cylindrical body having a space formed therein for accommodating a tubular container for containing a chemical agent and which has an outlet formed at its bottom end, the cylindrical body having an annular cylindrical space formed therein so as to open at an upper end surface thereof; a pusher comprising a handle portion for pressing a piston to be inserted into the tubular container, and a tubular body disposed on a side of the handle portion which presses the piston, wherein a circumferential surface of the tubular body and a circumferential surface of the cylindrical body which defines the annular cylindrical space are screw-threadedly engaged.

A second aspect of the invention provides a method for extruding a chemical agent using the chemical-agent extrusion assisting-tool defined above, comprising: rotating the handle portion so as to screw-engage the tubular body and the circumferential surface of the cylindrical body which defines the annular cylindrical space so as to press the piston into the tubular container, thereby extruding the chemical agent from the tubular container.

The tubular container for containing a chemical agent can be a syringe barrel generally used for filling or applying a chemical agent such as calcium-phosphate-based cement to a required location. Appropriate determination of the diameter and length of the columnar space of the tool body enables use of a container having a certain structure and dimensions, other than general syringe barrels.

The term "contain" as used herein includes the following two cases: a previously prepared chemical agent is filled into the tubular container; and powder and a kneading liquid, for example, calcium phosphate powder and a kneading liquid for preparation of calcium-phosphate-based cement, are mixed and kneaded within the tubular container.

Thus, a third aspect of the invention provides a kneader for use as a tubular container with the chernical-agent extrusion assisting-tool according to the first aspect, the kneader comprising: a cylinder to be accommodated in said space formed in the tool body and having a cylindrical portion and a nozzle portion formed at one end of the cylindrical portion; a plug disposed slidably within the cylindrical portion; a piston which includes a shaft portion extending through the plug for rotation relative thereto so as to cause movement of the piston axially of the cylinder, a kneading portion located at an end of the shaft between the plug and the nozzle portion, and a handle portion location at the other end of the shaft for engagement by the pusher; a stopper for releasably holding the plug at the other end of the cylindrical portion; and a cover removably attachable to the nozzle portion.

A fourth aspect of the invention provides a method for preparing and extruding a chemical agent using the kneader according to the third aspect and the chemical-agent extrusion assisting-tool according to the first aspect, comprising: introducing constituents to be mixed and kneaded to form the chemical agent into the cylinder of the kneader; turning the handle portion of the piston with the plug fixed by means of the stopper and the cover attached to the nozzle portion so as to rotate and axially move to the kneading portion within the cylindrical portion, and thereby to knead the constituents and form the chemical agent; fitting the cylinder into the space formed in the tool body with the kneading portion returned to said other end of the cylindrical portion adjacent to the plug and removing the cover from the nozzle portion; releasing the stopper; and rotating the handle portion of the pusher so as to screw-engage the circumferential surface of the tubular body and the circumferential surface of the cylindrical body which defines the annular cylindrical space so as to cause the pusher to press the piston and the released plug into the tubular container thereby extruding the previously kneaded chemical agent from the kneader.

The chemical-agent extrusion assisting-tool is useful for extruding those chemicals which the user encounters difficulty in extruding through, for example, an injection needle by pressing with his/her fingers. Examples of such chemicals include a bone cement and more particularly a calcium-phosphate-based cement. Calcium-phosphate-based cement is prepared from calcium phosphate powder and a kneading liquid. After setting, calcium phosphate powder is converted to hydroxyapatite. The thus-formed set substance has sufficient strength to serve as a prosthetic material for bone and exhibits excellent bio-compatibility and bio-activity. Accordingly, calcium-phosphate-based cement is useful for formation of, for example, artificial bone, artificial joints, and artificial tooth roots having excellent strength and bio-activity.

Examples of calcium phosphate powder include tetracalcium phosphate, calcium hydrogen phosphate, $\alpha$-tricalcium phosphate, and $\beta$-tricalcium phosphate. These powders may be used singly or in combination. Calcium phosphate powder may be mixed with X-ray contrast medium, such as barium sulfate or bismuth subcarbonate. In order to shorten setting time, hydroxyapatite or fluoride may be added as seed crystals.

Examples of the kneading liquid include water, such as pure water, and an aqueous solution which contains an appropriate amount of polysaccharide, such as dextran sulfate, an organic acid, or an inorganic acid.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

A method for accommodating in a tool body of a chemical-agent extrusion assisting-tool a tubular container which contains a chemical agent composed of calcium phosphate powder and a kneading liquid and for extruding the chemical agent from the tubular container will now be described in detail by way of an embodiment. However, the present invention should not be construed as being limited thereto.

(1) Structure of Chemical-Agent Extrusion Assisting-Tool

Figure 1:
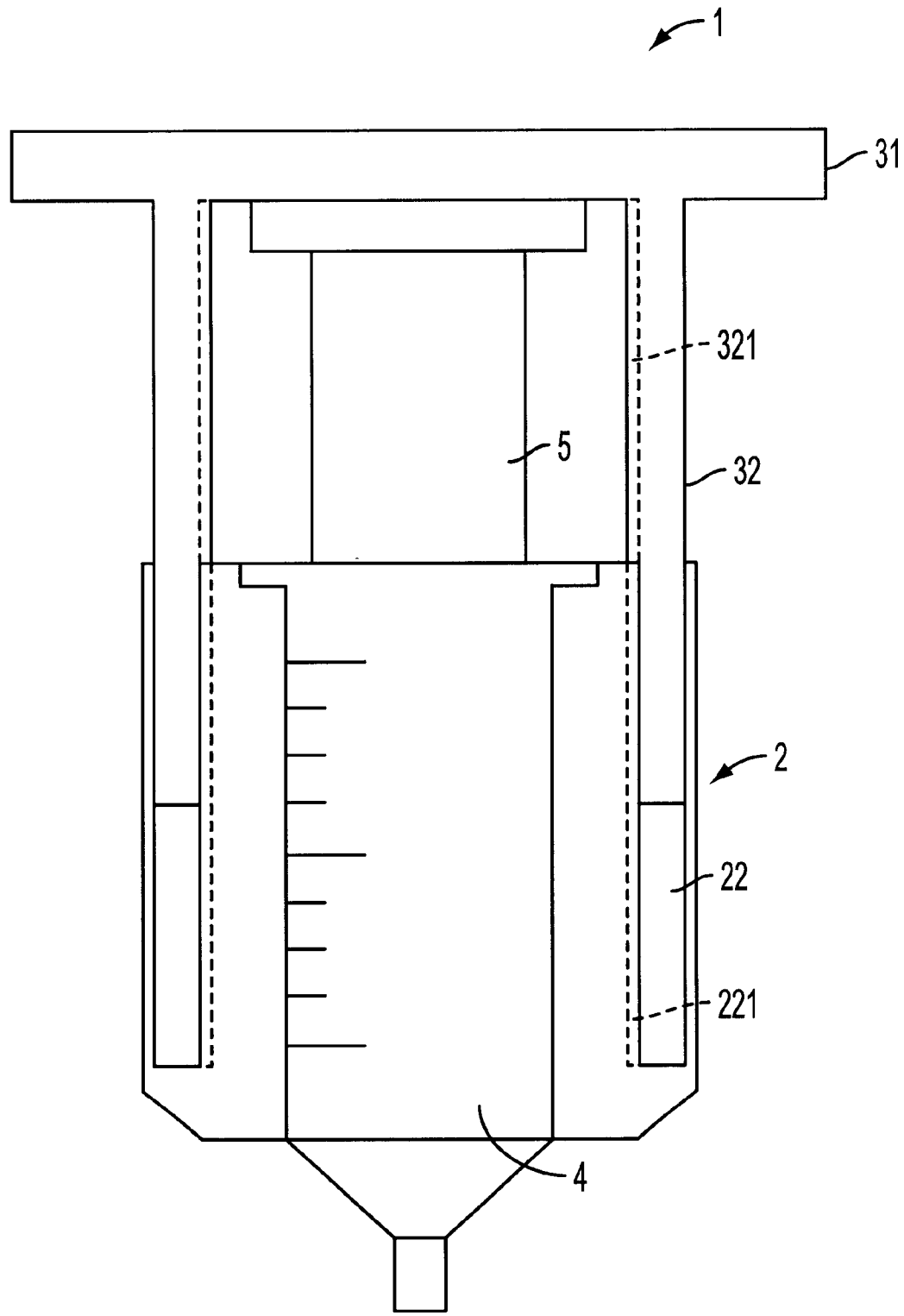
FIG. 1 is a schematic view of a chemical-agent extrusion assisting-tool in accordance with the invention.
Figure 2:
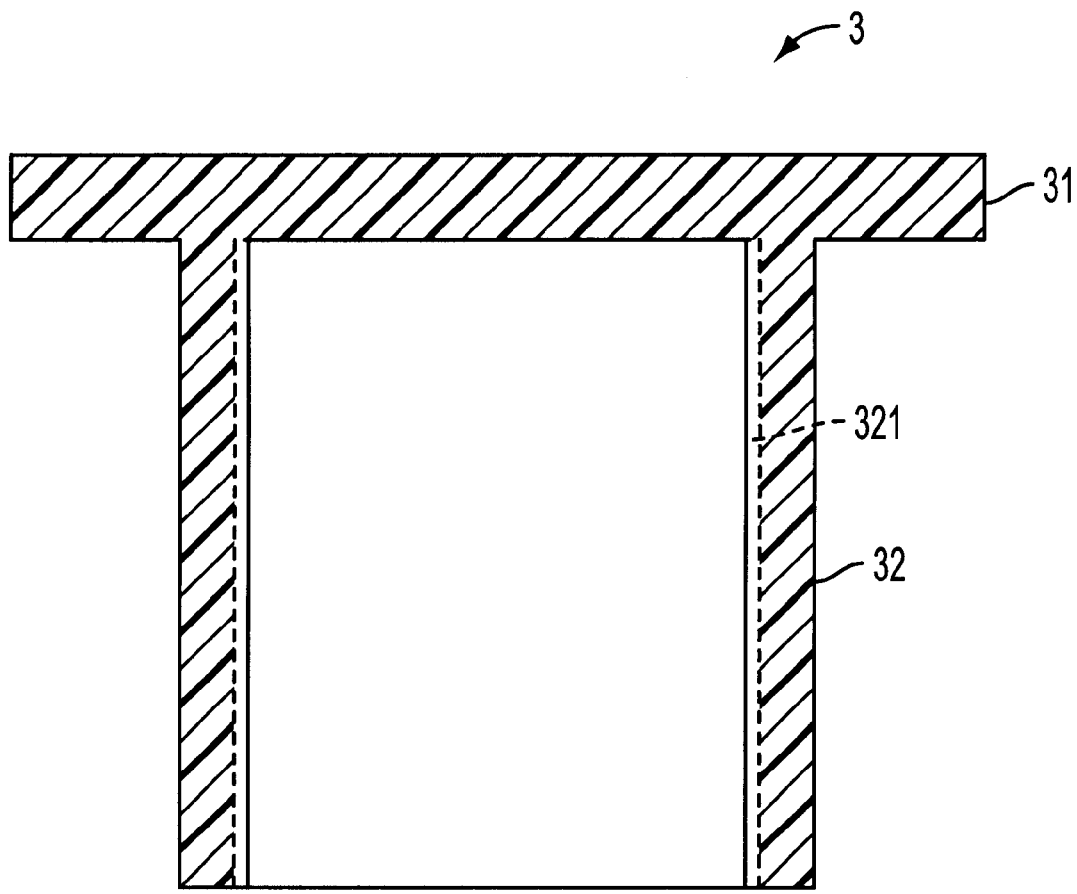
FIG. 2 is a longitudinal sectional view of a pusher of the chemical-agent extrusion assisting-tool shown in FIG. 1.
Figure 3:
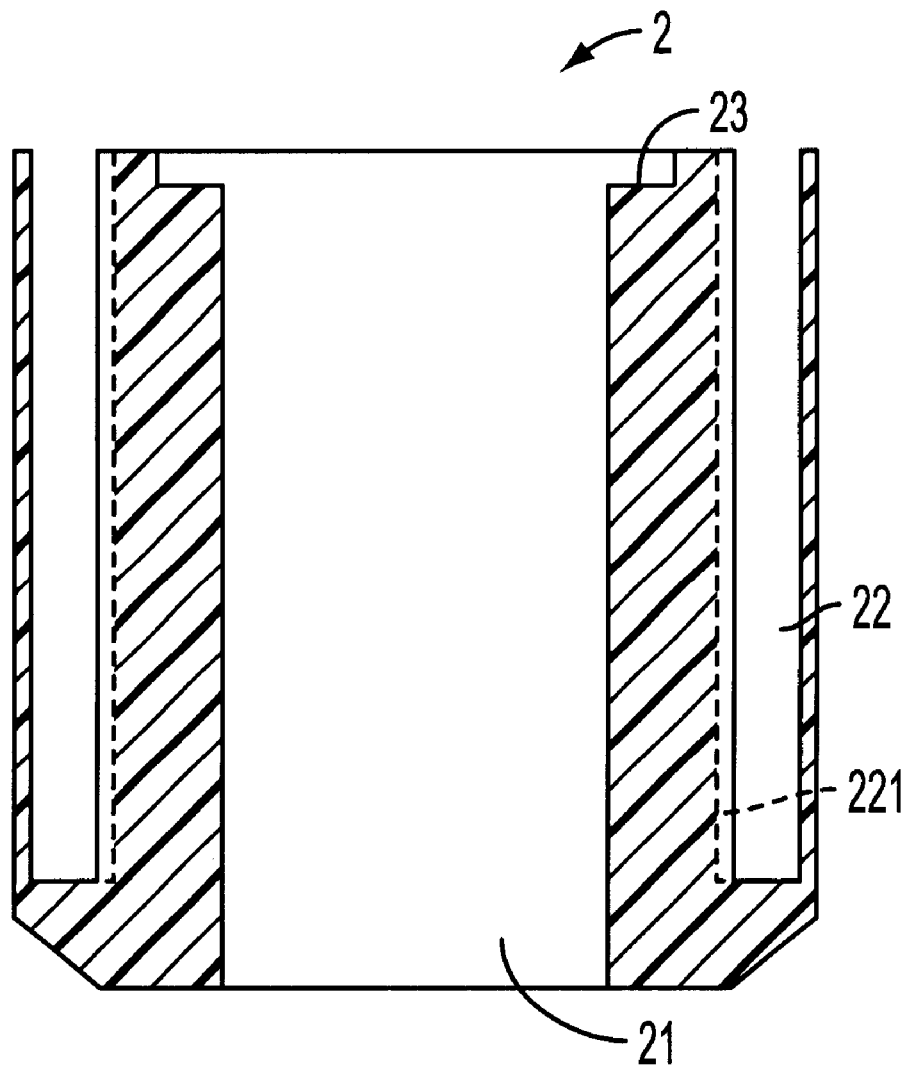
FIG. 3 is a longitudinal sectional view of a tool body of the chemical-agent extrusion assisting-tool shown in FIG. 1.

With reference to FIGS. 1 to 3, a chemical-agent extrusion assisting-tool 1 includes a tool body 2 in the form of a cylindrical body. A tubular container 4 is accommodated within a columnar cylindrical space 21 formed in a central portion of the tool body 2. The diameter of the space 21 and the outside diameter of the tubular container 4 are determined preferably such that the tubular container 4 can be readily accommodated within the space 21 while sliding on the inner circumferential surface of the cylindrical body and such that the accommodated tubular container 4 is free of play. Preferably, a recess 23 is formed around the upper end edge of the inner circumferential surface defining the space 21. The recess 23 is adapted to prevent the tubular container 4 from slipping out of the space 21. More preferably, the recess 23 assumes a form which corresponds to the shape of a flange of the tubular container 4 and which prevents the tubular container 4 from rotating together with a pusher 3 when the pusher 3 is rotated. An annular cylindrical space 22 encircling the columnar cylindrical space 21 opens at the upper end surface of the cylindrical body; i.e., at the end surface of the cylindrical body from which the tubular container 4 is inserted thereinto. The annular cylindrical space 22 extends to a predetermined depth longitudinally within the cylindrical body. The predetermined depth is determined such that a piston 5 can be inserted sufficiently into the tubular container 4 to ensure complete extrusion of a chemical agent therefrom.

The pusher 3 includes a handle portion 31 and a tubular body 32. The handle portion 31 and the tubular body 32 may be formed separately and then be fixedly secured together by an appropriate method; for example, by screw engagement or bonding by means of an adhesive. From the viewpoint of strength, however, it is preferable that the handle portion 31 and the tubular body 32 be integrally formed. A circumferential surface 321 of the tubular body 32 is screw-threadedly engaged with a circumferential surface 221 of the cylindrical body which defines the cylindrical space 22 of the tool body 2. As in the case of the depth of the cylindrical space 22, the length of the tubular body 32 is determined preferably such that the piston 5 can be inserted sufficiently into the tubular container 4 to ensure complete extrusion of a chemical agent.

Figure 4:
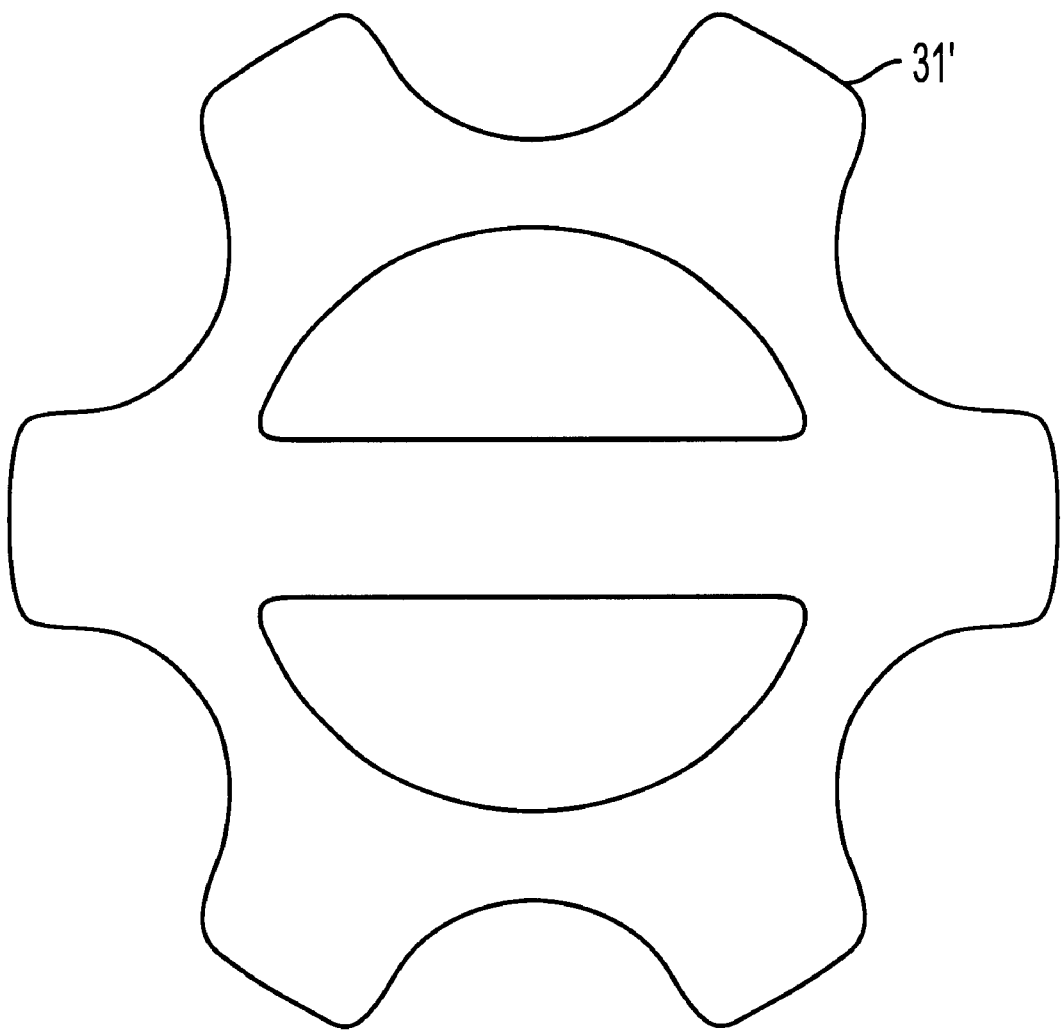
FIG. 4 is a top view showing an example of a handle portion of the pusher of FIG. 2.

In order to facilitate rotation, the side surface of the handle portion 31 is preferably knurled against slip, as shown at 31' in FIG. 4. Since the handle portion 31 of larger diameter requires a smaller force to rotate, it is preferable that the handle portion 31 assume as large a diameter as possible so long as no inconvenience to the user occurs during use. The handle portion 31 may assume the form of a disk. However, in order to facilitate rotation and reduce the weight of the pusher 3, the handle portion 31 may assume an apertured form as shown in FIG. 4.

Thus, a circumferential surface of the cylindrical body which defines the annular cylindrical space 22 of the tool body 2 is screw-threadedly engaged with a circumferential surface of the tubular body 32. Rotation of the handle portion 31 causes the tubular body 32 to enter the cylindrical space 22 formed in the cylindrical body. Also, the piston 5 pressed by the handle portion 31 is inserted into the tubular container 4, thereby extruding a chemical agent. Either one of the two circumferential surfaces of the cylindrical body which define the annular cylindrical space 22, and the corresponding inner or outer circumferential surface of the tubular body 32 are threaded. Making the pitch of the threads finer reduces a force required to depress the piston 5. Making the pitch coarser increases the speed of depressing. Accordingly, the pitch is selected preferably from within a range of 1 to 20 mm, particularly preferably from within a range of 3 to 10 mm, according to, for example, the viscosity of a chemical agent contained in the tubular container 4.

The material of the tool body 2 and that of the pusher 3 are not particularly limited. Examples of such materials include resins and metals. Particularly, there is preferred a synthetic resin which has excellent moldability and which allows the entire tool body 2 to be formed easily and allows the pusher 3 to be formed easily such that the handle portion 31 and the cylindrical portion 32 are integral with each other. Examples of such a synthetic resin include polyamide; polystyrene; polycarbonate; polyolefin such as polyethylene and polypropylene; polyacetal; polyester; and acrylic resin.

Figure 5:
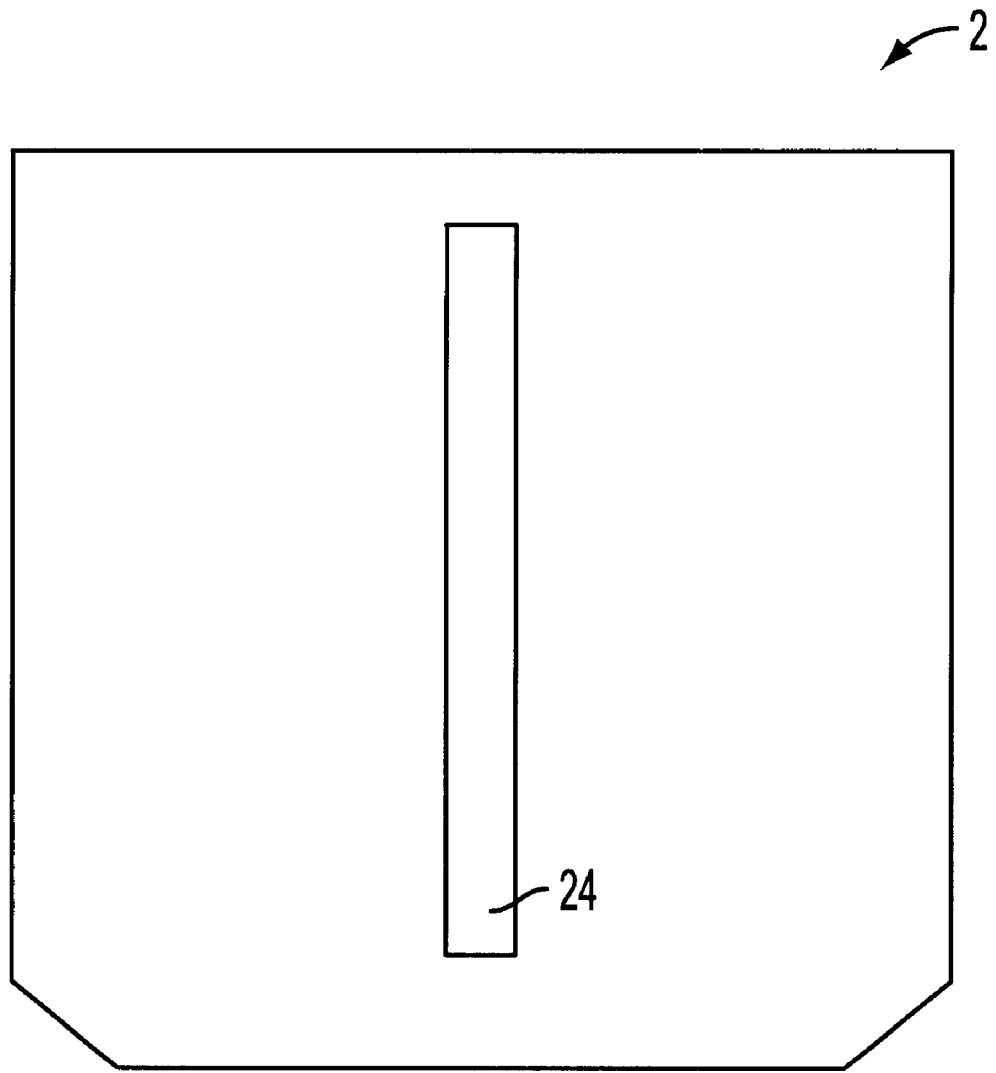
FIG. 5 is a front view of a form of the tool body of FIG. 3 having a window formed in its side wall.

In the above-described chemical-agent extrusion assisting-tool, even when the tool body 2 is opaque, the amount of extrusion can be estimated by observing of the position and movement of the piston 5 to be inserted into the tubular container 4. Preferably, however, the tool body 2 and the pusher 3 are formed of a transparent synthetic resin, such as polycarbonate or acrylic resin, so that the amount of extrusion of a chemical agent can be easily confirmed. Alternatively, as shown in FIG. 5, a narrow window 24 may be formed in the side wall of the tool body 2, the size of the window being such as not to affect the strength of the tool body 2, whereby the amount of extrusion can be viewed therethrough. Further, graduations may be formed along the window 24 so as to facilitate confirmation of the amount of extrusion. Also, different color tones may be imparted to the tool body 2 and the pusher 3 to thereby improve visibility.

(2) Extrusion of Calcium-Phosphate-Based Cement using the Chemical-Agent Extrusion Assisting-Tool

EXAMPLE 1

Using a commercially available syringe barrel as a tubular container, calcium-phosphate-based cement was extruded according to the following procedure.

Calcium-phosphate-based cement, which has a particularly high viscosity, was used as the contents of the tubular container to be extruded. An equimolar mixture of tetracalcium phosphate powder and dicalcium phosphate powder was used as the calcium phosphate powder. Pure water which contained sodium dextran sulfate was used as a kneading liquid. The liquid/powder ratio (the amount ratio of kneading liquid to powder) was 0.3 on the basis of weight.

First, the mixed powder of calcium phosphate and the kneading liquid were placed in a mortar. The resultant mixture was kneaded using a pestle. The kneaded cement was filled into the syringe barrel. The syringe barrel that was used was a commercially available one having a capacity of 10 milliliters (product of Terumo Corp). An injection needle that was used was a commercially available, disposable Luer-Lok™ injection needle (18G) (product of Becton, Dickinson & Co.). Next, the syringe barrel was accommodated within the columnar space formed in the tool body. A flange portion of the syringe barrel was placed in the recess 23 formed around the upper end edge of the inner circumferential surface of the tool body 2, thereby preventing the syringe barrel from slipping out of the tool body. Subsequently, the Luer-Lok™ injection needle of 18G was connected to an outlet portion of the syringe barrel. Then, the tubular body 22 of the pusher was fitted into the annular cylindrical space 22 formed in the tool body through screw engagement. The handle portion was rotated so as to advance the tubular body into the annular cylindrical space, thereby pressing the piston 5 into the syringe barrel by means of the handle portion and thus, extracting the kneaded cement through the injection needle.

Thus, in contrast to a failure in inserting the piston when insertion was attempted by pressing with fingers, use of the above described chemical-agent extrusion assisting-tool enabled the user to extrude the kneaded cement very easily. Also, the kneaded cement was extruded completely without any remaining within the syringe barrel.

EXAMPLE 2

In place of the commercially available syringe barrel, a specific kneader, to be described below, was used. Calcium phosphate powder and a kneading liquid were mixed and kneaded using the kneader, to thereby prepare a kneaded cement. Subsequently, the kneader was accommodated within the tool body 2 of the chemical-agent extrusion assisting-tool 1, followed by extrusion of the kneaded cement. Calcium phosphate powder and the kneading liquid were similar to those used in Example 1. The structure of the chemical-agent extrusion assisting-tool was similar to that in the case of Example 1. Dimensions of the chemical-agent extrusion assisting-tool were determined so as to be compatible with the kneader.

(3) Structure of Kneader

Figure 6:
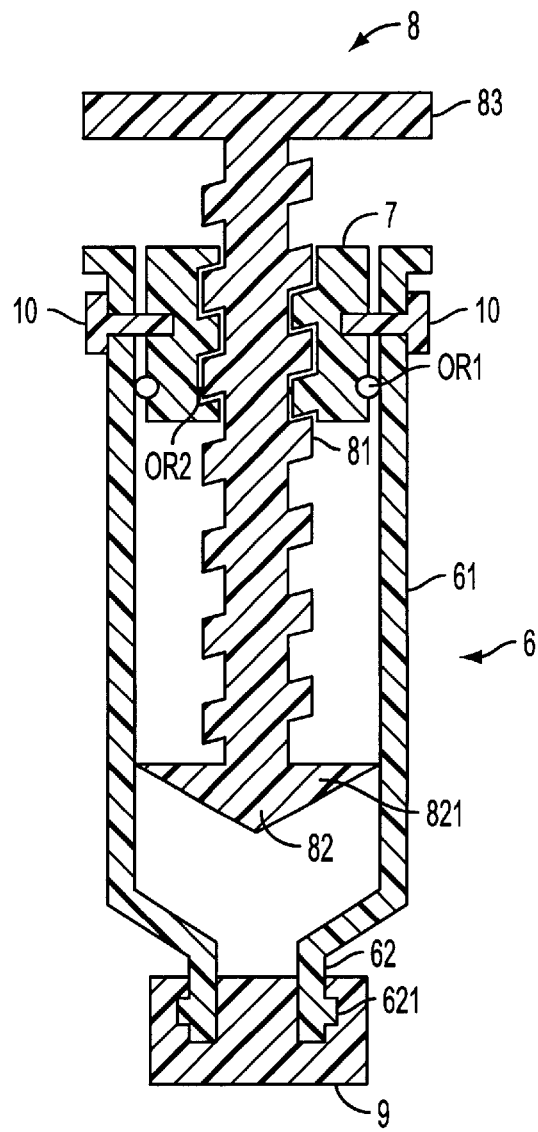
FIG. 6 is a sectional view of a kneader incorporating a stirring blade forkneading calcium-phosphate-based cement.
Figure 6A:
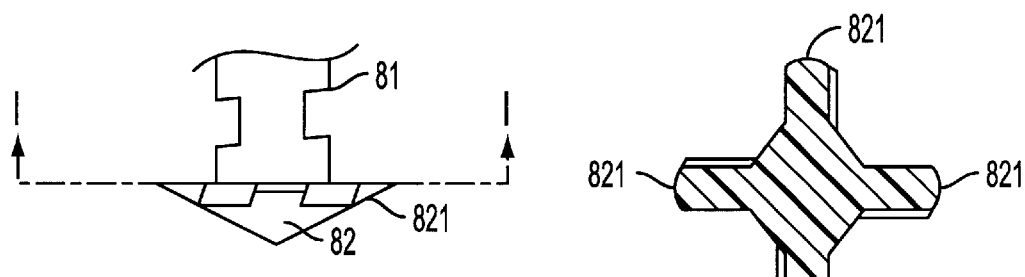
FIG. 6(a) is a side view showing a portion of the stirring blade of the kneader shown in FIG. 6.
Figure 6B:
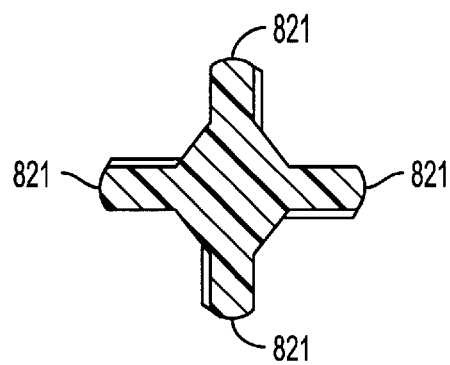
FIG. 6(b) is a sectional view of the stirring blade taken along line I—I of FIG. 6(a)
Figure 7:
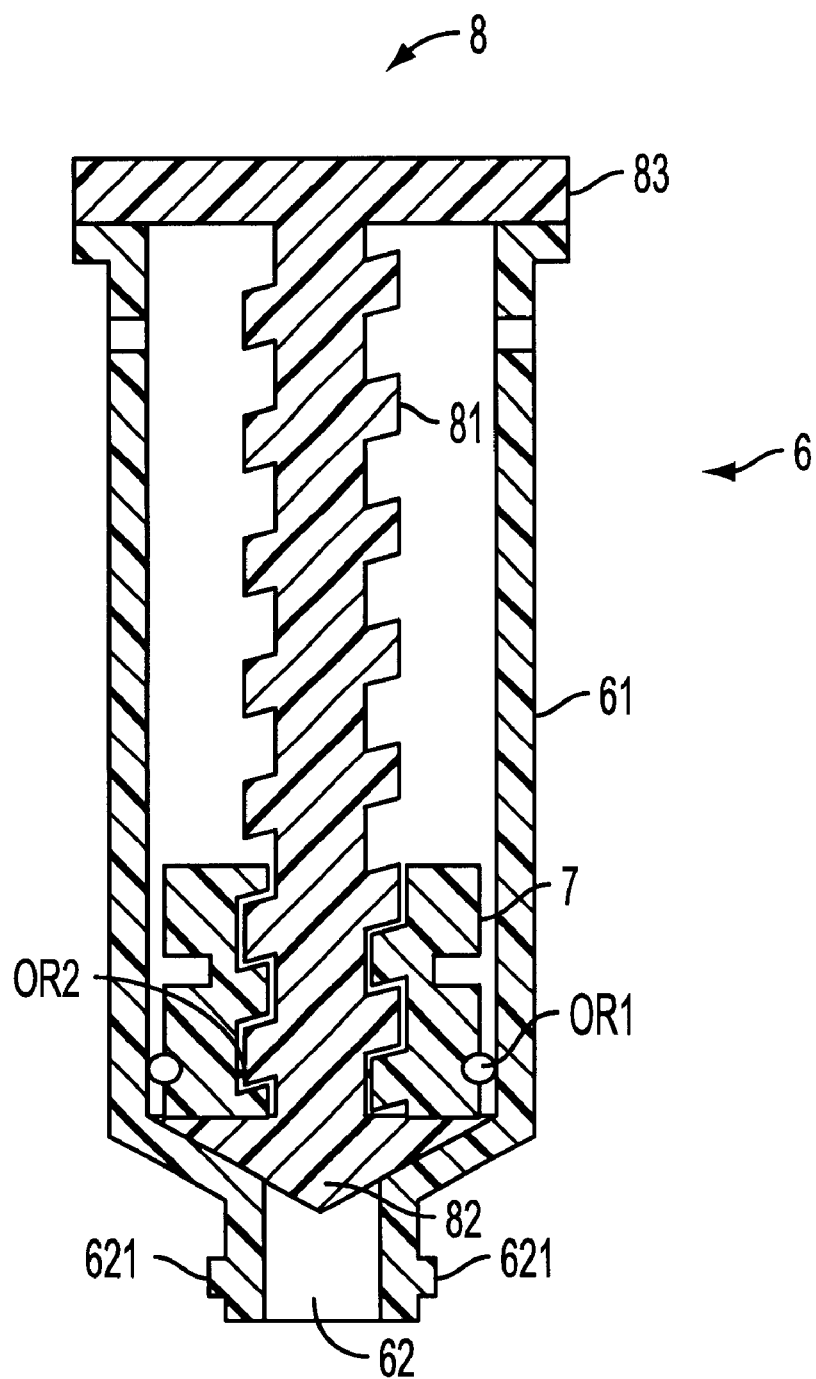
FIG. 7 is a sectional view showing the kneader of FIG. 6 after having completed extrusion.

The specific structure of the kneader used in the above Example 2 will next be described with reference to FIGS. 6 and 7.

The kneader includes a cylinder 6, a plug 7, a piston 8, a cover 9, and stoppers 10. The cylinder 6 includes a cylindrical portion 61 and a nozzle portion 62 formed at one end of the cylindrical portion 61. The plug 7 is disposed slidably within the cylindrical portion 61. The piston 8 includes a shaft portion 81 extending rotatably through the plug 7 and disposed in a vertically movable manner; a kneading portion 82 located at one end of the shaft portion 81; and a handle portion 83 located at the other end of the shaft portion 81. The cover 9 is fitted to an end of the nozzle portion 62 of the cylinder 6. The stoppers 10 are adapted to fix the plug 7 at the other end of the cylindrical portion 61. The kneading portion 82 includes stirring blades 821 extending laterally and arranged circumferentially.

In the kneader which was actually used, the cylinder 6 had a length of about 90 mm and an outside diameter of about 25 mm, and about 10 ml of contents could be kneaded therein. The amount of cement that can be kneaded within the cylinder 6 is preferably equal to or slightly greater than the amount of cement to be consumed in a single phase of treatment (for example, when the amount of cement to be consumed in a single phase of treatment is 10 ml, the amount of cement to be kneaded in the cylinder capacity of 20 ml may be 10–13 ml). If the capacity of the cylinder 6 is less than the amount of cement to be consumed in a single phase of treatment, kneading must be performed several times. If the amount of the cement to be kneaded in the cylinder 6 is in excess of the amount of cement to be consumed in a single phase of treatment, waste of kneaded cement will result.

The plug 7 assumes a substantially columnar form. The plug 7 is inserted into the cylinder 6 through an opening of the cylinder 6 and is fixed in place by means of the stoppers 10. Internal threads are formed on the wall surface of a through-hole formed centrally of the plug 7. Reception holes for receiving the corresponding stoppers 10 are formed in the side wall of the plug 7. Grooves are formed circumferentially in the outer circumferential surface and in the internally-threaded inner circumferential surface of the plug 7. O-rings OR1 and OR2 of silicone resin are fitted into the grooves, respectively. The 0-rings fitted to sliding portions of the plug 7 prevent escape of the kneaded cement from the kneader and entry of germs into the kneader, and facilitate sliding of the plug 7 and rotation of the shaft portion 81.

The piston 8 includes the shaft portion 81, the kneading portion 82, the stirring blades 821, and the handle portion 83. The shaft portion 81 assumes the form of an externally-threaded column. The external thread of the shaft portion 81 engages the internal thread of the plug 7, whereby rotation of the shaft portion 81 causes the piston 8 to move vertically within the cylinder 6. Rotation of the shaft portion 81 also causes the kneading portion 82 located at one end of the shaft portion 81 to move vertically. Also, when the stoppers 10 are removed, the shaft portion 81 can be moved vertically without rotation to thereby move the plug 7 vertically lengthwise within the cylinder 6.

The kneading portion 82 is located at an end of the shaft portion 81. As shown in FIGS. 6(*a*) and 6(*b*), the kneading portion 82 includes four stirring blades 821, which extend radially from the center of the kneading portion 82. The stirring blades 821 may be arranged to incline with respect to the center axis of the kneading portion 82. The extension lines of the corresponding stirring blades 821 pass through the center of the kneading portion 82; however, the stirring blades 821 may be arranged such that their extension lines do not pass through the center of the kneading portion 82. Each of the stirring blades 821 has a substantially wedge-like section; i.e., the thickness of the stirring blade 821 decreases toward its tip end. The shaft portion 81 is externally threaded preferably at a pitch of 5–25 mm, more preferably at a pitch of 6–20 mm, and particularly preferably at a pitch of 7–15 mm. By using such a thread pitch range, homogeneously kneaded cement can be easily prepared within a short period of time. The number of stirring blades can be 2 to 6, thereby imparting various structures to the kneading portion 82 for efficient kneading.

The handle portion 83 assumes the form of a disk, the center of which is fixedly attached to the other end of the shaft portion 81. With the kneader fitted into the chemical-agent extrusion assisting-tool, the lower surface of the handle portion 31 of the pusher 3 of the chemical-agent extrusion assisting-tool 1 presses the upper surface of the handle portion 83 so as to move the piston 8 and the plug 7 toward the nozzle portion 62 of the cylinder 6, thereby extruding kneaded cement from the cylinder 6. The handle portion 83, the shaft portion 81, and the kneading portion 82 may be formed separately and then be fixedly secured together by an appropriate method; for example, by screw engagement or bonding by means of adhesive. From the viewpoint of strength, however, it is preferable that these members be integrally formed.

The cover 9 is engaged with a protrusion 621, which is formed on the outer circumferential surface of the nozzle portion 62 of the cylinder 6 and constitutes a Luer-Lok™ structure. The thus-engaged cover 9 prevents escape of the contents of the cylinder 6 while powder and a kneading liquid are mixed and kneaded within the cylinder 6. Adapting the nozzle portion 62 to have a Luer-Lok™ form similar to that employed by a commercially available syringe barrel enables easy attachment to and detachment from the nozzle portion 62 of an injection needle or a catheter for use with a commercially available syringe.

Each of the stoppers 10 assumes the form of a pin for fixing the plug 7 in place within the cylinder 6 when extrusion is not performed. The stoppers 10 are inserted through the corresponding through-holes formed in the side wall of the cylinder 6 and into the corresponding reception holes formed in the side wall of the plug 7, thereby fixing the plug 7 within the cylinder 6 at a predetermined position. Two to six equally spaced stoppers 10 can be arranged circumferentially on the cylindrical portion. Particularly, an arrangement of two to four stoppers 10 is preferred.

This kneader can be easily manufactured and can be stored in a sterile state before use. Thus, the kneader may be used as a disposable instrument.

(4) Preparation of Calcium-Phosphate-Based Cement by using a Kneader

First, in order to prevent escape of the contents of the kneader through the nozzle portion 62 in the course of kneading, the cover 9 was fitted to the nozzle portion 62 so as to engage the protrusion 621, thereby blocking the opening portion of the nozzle portion 62. Subsequently, a predetermined amount of a mixed powder of calcium phosphate was placed into the cylinder 6, and then the plug 7 was fixed in place by means of the stoppers 10. The plug 7 and the piston 8 were mutually engaged beforehand. Specifically, the shaft portion 81 of the piston 8 was screw-engaged with the internally-threaded portion of the plug 7, and the kneading portion 82 was brought into contact with the plug 7.

Next, the kneader was irradiated with γ rays from the outside for sterilization of the contents thereof. The cover 9 was removed from the nozzle portion 62 in such a manner as not to cause escape of the mixed powder from the nozzle portion 62. Subsequently, a Luer-Lok™ syringe which contained a kneading liquid was connected to the nozzle portion 62 via a Luer-Lok™. The kneading liquid was injected into the kneader from the syringe. Then, the syringe was disconnected from the nozzle portion 62, and the cover 9 was replaced in an engaged manner to thereby resume blocking the nozzle portion 62. Subsequently, the kneader was gently shaken for 10–15 seconds. Then, the handle portion 83 was rotated so as to move the kneading portion 82 to the nozzle portion 62. Subsequently, the handle portion 83 was rotated in the reverse direction so as to move the kneading portion 82 to the plug 7. This reciprocating operation was repeated 3–10 times to thereby knead the mixed powder and the kneading liquid. Since this kneading work was performed within the closed kneader, entry of foreign matter or germs into the cement was prevented.

Figure 8A:
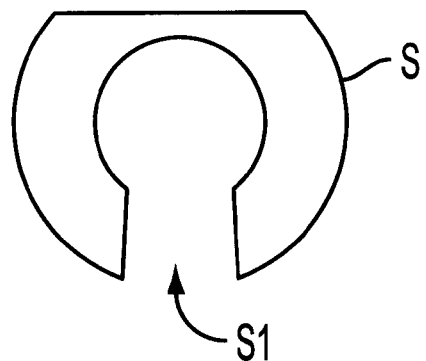
FIGS. 8(a) and 8(b) are, respectively, plan and front views of a whirl-stop member for preventing rotation of a piston when the pusher is rotated for extrusion of cement.
Figure 8B:
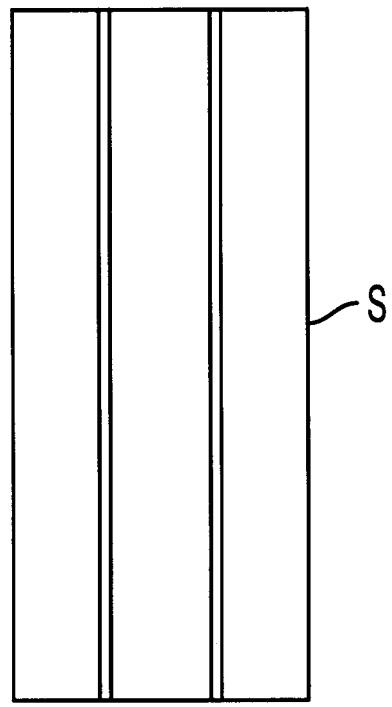

(5) Loading Tool Body of Chemical-Agent Extrusion Assisting-Tool with Kneader and Extrusion of Cement The piston 8 was raised until the upper surface of the kneading portion 82 came into contact with the lower surface of the plug 7. Then, the stoppers 10 were removed. Next, a whirl-stop member S shown in FIG. 8 was fitted to a portion of the piston 8 extending between the upper surface of the plug 7 and the lower surface of the handle portion 83, through a longitudinally extending opening portion SI thereof, to thereby prevent rotation of the piston 8 when the pusher 3 is rotated. Subsequently, the kneader was loaded into the tool body 2 of the chemical-agent extrusion assisting-tool 1, and the cover 9 was removed from the kneader. Calcium-phosphate-based cement was extruded in a manner similar to that of Example 1. As in the case of Example 1, use of the chemical-agent extrusion assisting-tool 1 enabled the user to extrude highly viscous cement, which could not be extruded simply by pressing with fingers; easily and completely.

While the present invention has been described with reference to the above embodiments, the present invention is not limited thereto. The present invention may be embodied in various other specific forms according to purposes or applications without departing from the scope of the invention. For example, a protrusion which projects radially inward may be formed at the lower-end edge of the inner circumferential surface of the cylindrical body which defines the space 21, so as to prevent the tubular container 4 from slipping out of the columnar space 21. Threads may be formed on the opposite circumferential surfaces of the cylindrical body which define the cylindrical space 22 in the tool body 2, and on both the inner and outer circumferential surfaces of the tubular body 32.

The above-described structure of the chemical-agent extrusion assisting-tool according to the first aspect of the invention enables the user to extrude a highly viscous chemical agent, such as calcium-phosphate-based cement, through an outlet of small diameter, such as an injection needle or a catheter. The chemical-agent extrusion assisting-tool can be of a disposable type, and thus can be used in surgical operations, which require use of sterilized instruments.

The extrusion method according to the second aspect of the invention enables the user to extrude a highly viscous chemical agent, such as calcium-phosphate-based cement, easily and completely through, for example, an injection needle or a catheter connected to a syringe barrel using the chemical-agent extrusion assisting-tool of the first aspect of the invention.

This application is based on Japanese patent application No. Hei. 11-285919 filed Oct. 6, 1999, which is incorporated herein by reference in its entirety.

What is claimed is:

1. A method for preparing and extruding a chemical agent using a kneader and a chemical-agent extrusion assisting-tool, said chemical-agent extrusion assisting-tool comprising:
a tool body in the form of a cylindrical body having a space formed therein for accommodating a tubular container which contains a chemical agent and which has an outlet formed at its bottom end, the cylindrical body having an annular cylindrical space formed therein so as to open at an upper end surface thereof; and
a pusher comprising a handle portion for pressing a piston to be inserted into the tubular container, and a tubular body disposed on a side of the handle portion which presses the piston;
wherein a circumferential surface of the tubular body and a circumferential surface of the cylindrical body which defines the annular cylindrical space are screw-threadedly engaged,
said kneader comprising:
a cylinder to be accommodated in said space formed in the tool body and having a cylindrical portion and a nozzle portion formed at one end of the cylindrical portion;
a plug disposed slidably within the cylindrical portion;
a piston which includes a shaft portion extending through the plug for rotation relative thereto so as to cause movement of the piston axially of the cylinder, a kneading portion located at an end of the shaft between the plug and the nozzle portion, and a handle portion location at the other end of the shaft for engagement by the pusher;
a stopper for releasably holding the plug at the other end of the cylindrical portion; and
a cover removably attached to the nozzle portion, and
the method comprising:
introducing constituents to be mixed and kneaded to form the chemical agent into the cylinder of the kneader;
turning the handle portion of the piston with the plug fixed by means of the stopper and the cover attached to the nozzle portion so as to rotate and axially move to the kneading portion within the cylindrical portion, to thereby knead the constituents and form the chemical agent;
fitting the cylinder into the space formed in the tool body with the kneading portion returned to said other end of the cylindrical portion adjacent to the plug and removing the cover from the nozzle portion;
releasing the stopper; and
rotating the handle portion of the pusher so as to screw-engage the circumferential surface of the tubular body and the circumferential surface of the cylindrical body which defines the annular cylindrical space so as to cause the pusher to press the piston and the released plug into the tubular container, thereby extruding the previously kneaded chemical agent from the kneader.

2. The method for preparing and extruding a chemical agent according to claim 1, wherein the chemical agent comprises bone cement.

3. The method for preparing and extruding a chemical agent according to claim 2, wherein the bone cement comprises a calcium-phosphate-based cement.

* * * * *